(12) United States Patent
Boime et al.

(10) Patent No.: US 7,442,376 B2
(45) Date of Patent: *Oct. 28, 2008

(54) GLYCOPROTEIN HORMONE COMPOSITIONS CONTAINING TWO β SUBUNITS

(75) Inventors: Irving Boime, St. Louis, MO (US); David Ben-Menahem, St. Louis, MO (US)

(73) Assignee: Washington University, St. Louis, MO (US)

( * ) Notice: Subject to any disclaimer, the term of this patent is extended or adjusted under 35 U.S.C. 154(b) by 667 days.

This patent is subject to a terminal disclaimer.

(21) Appl. No.: 10/647,088

(22) Filed: Aug. 21, 2003

(65) Prior Publication Data

US 2004/0220088 A1 Nov. 4, 2004

Related U.S. Application Data

(63) Continuation of application No. 09/175,017, filed on Oct. 19, 1998, now Pat. No. 6,635,256.

(51) Int. Cl.
*C07K 14/59* (2006.01)

(52) U.S. Cl. ............... 424/195.11; 435/69.4; 435/69.7; 424/192.1; 424/194.1; 424/198.1; 530/398; 530/397

(58) Field of Classification Search ........................ None
See application file for complete search history.

(56) References Cited

U.S. PATENT DOCUMENTS

| 5,338,835 A | 8/1994 | Boime | ........................ | 530/398 |
| 5,420,247 A | 5/1995 | Gearing et al. | .............. | 530/350 |
| 5,705,484 A | 1/1998 | Thomason | .................... | 214/2 |

FOREIGN PATENT DOCUMENTS

| EP | 0 163 406 | 12/1985 |
| EP | 0 839 831 | 5/1998 |
| WO | WO 85/01959 | 5/1985 |
| WO | WO 90/09800 | 9/1990 |
| WO | WO 91/16922 | 11/1991 |
| WO | WO 92 22568 | 12/1992 |
| WO | WO 95/22340 | 8/1995 |
| WO | WO 96/05224 | 2/1996 |
| WO | WO 99/25849 | 5/1999 |

OTHER PUBLICATIONS

Duijkers, I J et al., "Follicular fluid hormone concentrations after ovarian stimulation using gonadotropin preparations with different FSH/LH ratios. I. Comparison of an FSH dominant and a purified FSH preparation." International journal of fertility and women's medicine (US) Sep. Oct. 1997, 42 (5) p.306 10(Abstract only).*
R.K. Hyde et al., Biology of Reproduction 54(Suppl. 1) :105, Abstract 193, 1996.*
D. Ben-Menahem et al., Abstract OR28-3 presented at Endo 98, Endocrine Society, 1998.*
G. De Rosa et al., Annales d'endocrinologie 48(6):468-472, 1987(Abstract only).*
T. Sugahara et al., PNAS 92:2041-2045, 1995.*
Bielinska, *J Cell Biol* (1990) 111:330a (Abstract 1844).
Boime et al., "Synthesis of Genetically Fused Single Chain Analog of Human Chorionic Gonadotropin: Implications for Drug Design and Structure-Function Relationships," *Proceeding of the Symposium: "The Ovary Regulation, Dysfunction and Treatment,"* 1106:25-27 (1996).
Campbell et al., "Conversion of Human Choriogonadotropin into a Follitropin by Protein Engineering", *Proc Natl Acad Sci* (1991) 88:760-764.
Chen and Okayama, "High-Efficiency Transformation of Mammalian Cells by Plasmid DNA", *Mol Cell Biol* (1987) 7:2745-2752.
Chen et al., "The Carboxy-Terminal Region of the Glycoprotein Hormone α-Subunit: Contributions to Receptor Binding and Signaling in Human Chorionic Gonadotropin" *Molec Endocrinol* (1992) 6:914-919.
Dayhoff et al., "A Model of Evolutionary Change in Proteins" *Atlas of Protein Sequences and Structure* (1972) 5:89-99.
Duijkers et al., "Follicular Fluid Hormone Concentrations After Ovarian Stimulation Using Gonadotropin Preparations with Different FSH/LH ratios. 1. Comparison of an FSH-Dominant and a Purified FSH Preparation," *International Journal of Fertility and Women's Medicine* (USA) 42(5):306-310 (1997) [abstract only].
Erickson et al., "Synthetic α-Subunit Peptides Stimulate Testosterone Production in Vitro by Rat Leydig Cells" *Endocrinology* (1990) 126:2555-2560.
Fares, "Design of a Long Acting Follitropin Agonist by Fusing the C-terminal Sequence of the Chorionic Gonadotropin β Subunit to the Follitropin" *Proc Natl Acad Sci USA* (1992) 89:4304-4308.
Keutmann, "Receptor Binding Regions of hLH and hCGβ-Subunit: Structural and Functional Properties" pp. 103-117, 1993.
LaPolt, "Enhanced Stimulation of Follicle Maturation and Ovulatory Potential by Long Acting Follicle-Stimulating Hormone Agonists with Extended Carboxyl-Terminal Peptides", *Endocrinology* (1992) 131:2514-2520.

(Continued)

*Primary Examiner*—Lorraine Spector
(74) *Attorney, Agent, or Firm*—Morrison & Foerster LLP

(57) ABSTRACT

Forms of differentially acting glycoprotein hormones are disclosed. These compositions are of the formula $$\beta^1\text{-(linker}^1)_m\text{-}\alpha\text{-(linker}^2)_n\text{-}\beta^2; \quad (1)$$

$$\beta^1\text{-(linker}^1)_m\text{-}\beta^2\text{-(linker}^2)_n\text{-}\alpha; \quad (2)$$

$$\alpha\text{-(linker}^1)_m\text{-}\beta^1\text{-(linker}^2)_n\text{-}\beta^2; \quad (3)$$

$$\beta^2\approx\alpha\text{-(linker)}_m\text{-}\beta^1; \text{ or} \quad (4)$$

$$\beta^1\text{-(linker)}_m\text{-}\alpha\approx\beta^2 \quad (5)$$

wherein each of $\beta^1$ and $\beta^2$ has the amino acid sequence of the β subunit of a vertebrate glycoprotein hormone or a variant of said amino acid sequence, as variants are defined herein. "α" designates the α subunit of a vertebrate glycoprotein hormone or a variant thereof, "linker" refers to a covalently linked moiety that spaces the $\beta^1$ and $\beta^2$ subunits at appropriate distances from the α subunit and from each other. "≈" is a noncovalent link. Each of m and n is independently 0 or 1.

7 Claims, No Drawings

OTHER PUBLICATIONS

Lapthorn, "Crystal Structure of Human Chorionic Gonadotropin" *Nature* (1994) 369:455-461.

Lustbader et al., EDS, *Springer Verlag* (New York) (1994) 122-134.

Matzuk et al., "Effects of Preventing O-glycosylation on the Secretion of Human Chorionic Gonadotropin in Chinese Hamster Ovary Cells", *Proc Natl Acad USA* (1987) 84:6354-6358.

Matzuk et al., "The Glycoprotein α-Subunit is Critical for Secretion and Stability of the Human Thyrotropin ꓱ-Subunit" *Mol Endocrinol* (1988) 2:95-100.

Matzuk and Boime, "The Role of the Asparagine-linked Oligosaccharides of the α Subunit in the Secretion and Assembly of Human Chorionic Gonadotropin" J Cell Biol (1988) 106:1049-1059.

Moyle et al., "Co-Evolution of Ligand-Receptor Paris" *Nature* (1994) 368:251-255.

Patel, "A Clasped Embrace" *Nature* 369:438-439, 1995.

Sachais et al., "Molecular Basis for the Species Selectivity of the Substance P Antagonist CP-96, 345" Biol Chem (1993) 268:2319.

Wu, H., "Structure of Human Chorionic Gonadotropin at 2.6 A Resolution from MAD analysis of the Selenomethionyl Protein" *Structure* (1994) 2:545-558.

Xiao-Chi et al., "Expression of Human Luteinizing Hormone (LH) and Chorionic Gonadotropin from Human but not Equine, Rat and Ovine Species" Endocrinol (1991) 5:759-768.

Yoo et al., "Conversion of Lysine 91 to Methionine or Glutamic Acid in Human Choriogonadotropin α Results in the Loss of cAMP Inducibility" *J Biol Chem* (1991) 266:17741-17743.

\* cited by examiner

GLYCOPROTEIN HORMONE COMPOSITIONS CONTAINING TWO β SUBUNITS

This Application is a continuation of U.S. Ser. No. 09/175,017, filed 19 Oct. 1998, and now U.S. Pat. No. 6,635,256. The contents of this document are incorporated herein by reference.

ACKNOWLEDGMENT OF GOVERNMENT SUPPORT

This invention was made in part with government support under NIH Contract No. NO1-HD-9-2922, awarded by the National Institutes of Health. The government has certain rights in this invention.

CROSS REFERENCE

This application is a continuation-in-part of the U.S. Ser. No. 08/971,439, filed 17 Nov. 1997, the contents of which are incorporated herein by reference

TECHNICAL FIELD

The invention relates to the field of protein engineering, specifically to modified forms of certain glycoprotein hormones which native forms occur normally as heterodimers. The invention concerns multiple domain complexes of chorionic gonadotropin (CG), thyroid stimulating hormone (TSH), luteinizing hormone (LH), and follicle stimulating hormone (FSH), wherein an a subunit covalently linked to a β subunit may associate with an additional β subunit or may be covalently linked to two β subunits. These multiple domain glycoprotein hormones can provide two or more effects or functions, or can behave like agonists and/or antagonists of the native hormones.

BACKGROUND ART

In humans, four important glycoprotein hormones (LH, FSH, TSH and CG) are heterodimers that have identical a subunits and differing β subunits. Three of these hormones are present in virtually all other vertebrate species as well; CG has so far been found only in primates and in the placenta and urine of pregnant mares.

PCT application WO90/09800, published 7 Sep. 1990, and incorporated herein by reference, describes a number of modified forms of these hormones. One important modification is C-terminal extension of the β subunit by the carboxy terminal peptide (CTP) of human chorionic gonadotropin or a variant thereof. Other muteins of these hormones are also described. CTP is the sequence of amino acids extending from any one of positions 112-118 to position 145 of the β subunit of human chorionic gonadotropin. The PCT application describes variants of the CTP extension obtained by conservative amino acid substitutions such that the capacity of the CTP to alter the clearance characteristics of the hormone is not destroyed. In addition, PCT application WO94/24148 published 27 Oct. 1994, incorporated herein by reference, describes modifying these hormones by extension or insertion of the CTP at locations other than the C-terminus and CTP fragments shorter than the sequence extending from positions 112-118 to 145.

The CTP-extended β subunit of FSH is also described in two papers by applicants herein: LaPolt, P. S. et al.; *Endocrinology* (1992) 131:2514-2520 and Fares, F. A. et al.; *Proc Natl Acad Sci USA* (1992) 89:4304-4308. Both of these papers are incorporated herein by reference.

The crystal structure of human chorionic gonadotropin has been published in more or less contemporaneous articles; one by Lapthorn, A. J. et al. *Nature* (1994) 369:455-461 and the other by Wu, H. et al. *Structure* (1994) 2:545-558. The results of these articles are summarized by Patel, D. J. *Nature* (1994) 369:438-439.

PCT application WO91/16922 published 14 Nov. 1991 describes a multiplicity of chimeric and otherwise modified forms of the glycoprotein hormones. In general, the disclosure is focused on chimeras of α subunits or β subunits involving portions of various α or β chains respectively. One construct simply listed in this application, and not otherwise described, fuses substantially all of the β chain of human chorionic gonadotropin to the β subunit preprotein, i.e., including the secretory signal sequence for this subunit.

Two additional published PCT applications describe single-chain forms of these glycoprotein hormones wherein the α and β subunits are covalently linked to result in a compound of the general formula:

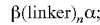
β(linker)$_n$α;

or

α(linker)$_n$β wherein n is 0 or 1 and α and β represent the respective subunits of these hormones: Moyle, W. R., PCT application WO95/22340 published 24 Aug. 1995 and the application of the inventor herein, WO96/05224 published 22 Feb. 1996. The disclosure of these documents is also incorporated herein by reference.

Forms of the above-described single-chain forms of these hormones in which the number of cystine bridges has been depleted are disclosed in U.S. Ser. No. 08/933,693 filed 19 Sep. 1997, and incorporated herein by reference.

The α subunit of a single-chain form of a glycoprotein hormone, CGβ-α, was found to bind noncovalently to an FSHβ subunit as disclosed by the applicants in Society for the Study of Reproduction, Abstract 193, 1996.

Recently, the α subunit of the single-chain glycoprotein hormone, FSHβ-α, was found to form a noncovalent link with a GCβ subunit as disclosed by the applicants in Endocrine Society, Abstract OR28-3, 1998.

It has now been found possible to use these glycoprotein hormones which have enhanced agonist and/or antagonist activity and/or which are multi-functional by either covalently linking an additional β subunit to a single-chain hormone or noncovalently linking an additional β subunit to the tethered α subunit of a single-chain hormone to mimic a natural hormone profile and/or control hormone ratios. These differentially acting glycoprotein hormones and their therapeutic uses for treating disorders such as polycystic ovarian disease, infertility, and ovarian hyperstimulation are disclosed hereinbelow.

DISCLOSURE OF THE INVENTION

The invention provides differentially acting glycoprotein hormones containing an α subunit covalently linked to a β subunit to form a single-chain hormone and an additional β subunit either covalently linked to the single-chain hormone or noncovalently linked to the tethered a subunit of the single-chain hormone. The compositions of the invention may either be glycosylated, partially glycosylated, or nonglycosylated and the fused α and β chains that occur in the native glycoprotein hormones or variants of them may optionally be linked through a linker moiety. Particularly preferred linker moieties include the carboxy terminal peptide (CTP) unit either as a complete unit or a variant including variants which represent only a portion thereof.

If the β subunits are the same, the compositions containing a noncovalently linked β subunit can act as agonists or antagonists, but the degree of activity may vary with time. This variation in the activity is due to the difference between the circulating half-lives of the covalently linked and the noncovalently linked β subunits. The circulating half-life of the noncovalently linked β subunit will inherently be shorter than that of the β subunit covalently linked to the α subunit. This is due to dissociation of the complex over time in the physiological environment; however, the covalently linked portion of the molecule remains an effective pharmaceutical.

For example, a composition having a FSHβ subunit covalently linked to an α subunit which is noncovalently linked to another FSHβ subunit would have a greater activity during the circulating half-life of the complex. However, the activity would decrease after the shorter half-life of the non-tethered FSHβ subunit ends.

A composition having a FSHβ subunit covalently linked to an α subunit which is noncovalently linked to a CGβ subunit would exhibit a longer circulating half-life for FSH activity and a shorter circulating half-life for CG activity. For the duration of the shorter circulating half-life, both the FSHβ and CGβ subunits would act upon their respective receptors. During the longer half-life, only the FSHβ subunit covalently linked to the α subunit would be active.

In all cases, if the β subunits are different, the compositions are bifunctional as agonists and/or antagonists. It will be noted that differential ratios of activity can be obtained by increasing or decreasing the agonist activity of one component relative to the other. For example, one could enhance the FSH/LH ratio by utilizing an FSH subunit with enhanced agonist activity and/or an LH subunit with decreased agonist activity.

In one aspect, the invention is directed to a method to provide different glycoprotein hormone activities to a subject in need of hormone regulation.

By a glycoprotein hormone "activity" is meant the ability to behave as an agonist or antagonist of a corresponding native hormone with the same or different biological half-life. Thus, "two different glycoprotein hormone activities" means that the activities conferred on the composition by each β subunit differ in one or more ways. One may be an agonist, the other an antagonist; one may be modified so as to provide enhanced activity; one may be modified so as to provide reduced activity; one may correspond to the activity of LH and the other to that of FSH, or one may have a long circulating half-life and the other a shorter circulating half-life. Thus, by providing different native β subunits in the compositions of formulas (1)-(5) or by providing variants of these β subunits, a wide variety of different glycoprotein hormone activities may be obtained.

In another aspect, the invention is directed to a glycosylated or nonglycosylated protein of the formula:

　(1);

　(2);

　(3);

　(4);

or

　(5)

wherein each of $\beta^1$ and $\beta^2$ has the amino acid sequence of the β subunit of a vertebrate glycoprotein hormone or a variant of said amino acid sequence, wherein said variants are defined herein. "α" designates the α subunit of a vertebrate glycoprotein hormone or a variant thereof; "linker" refers to a covalently linked moiety that spaces the $\beta^1$ and $\beta^2$ subunits at appropriate distances from the a subunit and from each other. "≈" is a noncovalent link. Each of m and n is independently 0 or 1.

In all of the foregoing cases, the compositions of the invention preserve conformation so that inclusion of the entire subunits in the compositions is unnecessary. Thus, the invention includes compositions of formulas (1)-(5) that comprise fragments of the α and/or β subunits wherein these forms retain the biological activity exhibited by the corresponding forms which contain the complete subunits.

It will be noted that the compounds of formulas (1)-(5) could further be modified to contain additional covalently linked β subunits. Thus, compounds of formulas (2) or (3) may be associated noncovalently with an additional β subunit; the compositions of formulas (4) or (5) may contain additional β subunits in the covalent chain. In addition, other non-covalent associations, such as that of a β-β dimer with α or an α-α dimer with β, could be employed.

In other aspects, the invention is directed to methods to produce the compositions of the invention, to pharmaceutical formulations containing the compositions of formulas (1)-(5), and to methods for their use. Antibodies specific for these compositions are also included in the invention.

MODES OF CARRYING OUT THE INVENTION

Four "glycoprotein" hormones in humans provide a family which includes human chorionic gonadotropin (hCG), follicle stimulating hormone (FSH), luteinizing hormone (LH), and thyroid stimulating hormone (TSH). As used herein, "glycoprotein hormones" refers to all the members of this family as they occur in humans and other vertebrates. All of these native hormones are heterodimers comprised of α subunits which, for a given species, are identical in amino acid sequence among the group, and β subunits which differ according to the member of the family. Thus, normally these native glycoprotein hormones occur as heterodimers composed of α and β subunits that are associated but not covalently linked. Most vertebrates produce FSH, TSH and LH; chorionic gonadotropin has been found only in primates, including humans, and in pregnant mares.

In animals, the α and β subunits of each hormone are encoded in different genes and are synthesized separately and then assembled into the noncovalent heterodimeric complex. In the compounds of the invention, at least one β subunit is directly linked to the α subunit in a single-chain primary structure. The three dimensional conformation conferred by secondary and tertiary structural considerations is sufficiently similar to the native heterodimeric form to permit the functionality of the glycoprotein hormone represented by the β subunit to be exhibited. An additional β subunit is linked to this single chain either covalently (formulas (1)-(3)) or by a noncovalent link of the tethered α subunit to an additional β subunit.

By suitable variation of the structures of the β subunits, the compositions of the invention may have agonist and/or antagonist activity "corresponding" to that of the native hormone; for example, the compounds may exhibit antagonist activity with respect to a receptor for one of the glycoprotein hormones, but agonist activity for the receptor of another, or may have agonist or antagonist activity for both. The spectrum of the activities exhibited by the compounds of the invention will be dependent on the selection of the individual α and β subunits and the variants employed as well as the nature of the linker moieties and the orientation of the α and β subunits.

In the compounds of formulas (1), (2) or (3), all three of the subunits are covalently linked; the compositions of formulas (4) and (5) contain a single chain β-α or α-β covalently linked dimer. The covalent linkage in each case is proximal to the N- or C-terminus of each subunit and may, in the case of any two subunits, may be head-to-head (i.e., proximal to the N-terminus of both components), tail-to-tail (i.e., proximal to the C-terminus of both components), or, most preferably, head-to-tail, wherein the N-terminus of one subunit is covalently linked to the C-terminus of the other. Fusion proteins which comprise head-to-tail linkages can readily be prepared using standard recombinant techniques provided all of the amino acids in the subunits and any linkers are encoded by the gene. Alternatively, the compounds of the invention can be prepared synthetically in which case, in addition to the head-to-tail configuration, linkers may be employed to bind the subunits proximal to their respective termini. Bifunctional linkers, including both heterobifunctional and homobifunctional types, are available from Pierce Chemical Company, Rockford, Illinois. Linkers which provide capacity to link two amino groups, or two carboxyl groups, or a carboxyl group and an amino group are available. If the linkage is not precisely at the N-terminus, an amino acid which provides a functional group containing side-chain will be required at a position proximal to the terminus to be linked.

Thus, preferred embodiments of the invention, the compounds of formulas (1), (2) or (3) are fusion proteins wherein the α and β subunits are linked head-to-tail either directly or through peptide linkers, where only gene-encoded amino acids comprise the sequence. These can be synthesized recombinantly. In another preferred embodiment of the invention, the compositions of formulas (4) and (5) comprise a single-chain form wherein the α and β subunits are linked head-to-tail either directly or through peptide linkers and an additional β subunit noncovalently linked to the tethered α subunit, where only gene-encoded amino acids comprise the multiple domain complex. This complex, too, can be synthesized recombinantly. However, it is unnecessary to restrict the compositions of the invention in this manner; the α and β subunits as well as the linkers may include amino acids that are not gene encoded. In addition, the linkers may be other than peptide-such as dicarboxylic acids or anhydrides, diamines, or bifunctional linkers such as those sold by Pierce Chemical Co., Rockford, IL and the like. In addition, the subunits of the single-chain form may be linked either directly or through a linker in a head-to-head or tail-to-tail configuration as well as a head-to-tail configuration as would be required in a fusion protein. Under these circumstances, for a head-to-head configuration, two amino groups may be linked through an anhydride or through any dicarboxylic acid derivative; two carboxyl groups can be linked through diamines or diols using standard activation techniques.

However, for convenience the most preferred form is a head-to-tail configuration wherein standard peptide linkages suffice and the single-chain form can be prepared as a fusion protein recombinantly or using synthetic peptide techniques either in a single sequence of reactions or, preferably, ligating individual portions of the entire sequence.

Whatever the embodiment, the α and β subunits are joined to the remainder of the molecule at positions proximal to their N and C termini. It is preferred that these subunits be linked directly at their termini, however this linkage may simply be "proximal." In general, "proximal" indicates a position that is in within 10 amino acids, preferably within five amino acids, more preferably within two amino acids of the terminus, and most preferably at the terminus per se. As noted above, where the linkage is other than at the N- or C-terminus per se, a side-chain functional group must be provided at a position proximal to the appropriate terminus.

The Subunit Components

As used herein, the common a subunit, and the FSH, LH, TSH, and CG βsubunits as well as the compositions of the invention have their conventional definitions and refer to the proteins having the amino acid sequences known in the art per se, or allelic variants thereof, regardless of the glycosylation pattern exhibited or other derivatization of the amino acid side chains.

"Native" forms of these peptides are those which have the amino acid sequences as are isolated from the relevant vertebrate tissue, and have these known sequences per se, or those of their allelic variants.

"Variant" forms of these proteins and of CTP units are those which correspond to the native subunit but have deliberate alterations, including truncations, in amino acid sequences of the native protein, produced by, for example, site-specific mutagenesis or by other recombinant manipulations, or which are prepared synthetically.

The resulting "variants" may behave as agonists or antagonists. The agonists may have enhanced activity as compared to the native form or diminished activity. By adjusting the level of activity in the two β subunits included in the compositions of the invention, variations in the effective ratios of hormones may be achieved. For example, by supplying an LH activity with diminished activity but a FSHβ subunit with native or enhanced activity, the ratio of FSH/LH activity can be enhanced.

The alterations that result in "variants" consist of 1-10, preferably 1-8, and more preferably 1-5 amino acid changes, including deletions, insertions, and substitutions, most preferably conservative amino acid substitutions. The resulting variants must retain an activity which affects the corresponding activity of the native hormone—i.e., either they must retain the biological activity of the native hormone to which they correspond so as to behave as agonists, or they must behave as antagonists, generally by virtue of being able to bind the receptors for the native hormones but lacking the ability to effect signal transduction.

"Conservative substitution" means, in the conventional sense, a substitution wherein the residue substituted is of the same general amino acid category as that for which substitution is made. Amino acids have been classified into such groups, as is understood in the art, by, for example, Dayhoff, M. et al., *Atlas of Protein Sequences and Structure* (1972) 5:89-99. In general, acidic amino acids fall into one group; basic amino acids into another; neutral hydrophilic amino acids into another; and so forth. More specific classifications are set forth in WO96/05224 incorporated by reference above.

One set of preferred variants is that wherein the glycosylation sites of either the α or β subunits or both have been altered. Some useful variants of the hormone quartet described herein are set forth in U.S. Pat. No. 5,177,193 issued 5 Jan. 1993, and incorporated herein by reference. As shown therein, the glycosylation patterns can be altered by destroying the relevant sites or, in the alternative, by choice of host cell in which the protein is produced.

Alterations in amino acid sequence also include both insertions and deletions. Thus, truncated forms of the hormones are included among variants, e.g., mutants of the α subunit which are lacking some or all of the amino acids at positions 88-92 at the C-terminus. In addition, α subunits with 1-10 amino acids deleted from the N-terminus are included.

Variants also include those with noncritical regions altered or removed. Such deletions and alterations may comprise entire loops, so that sequences of considerably more than 10 amino acids may be deleted or changed. The resulting variants must, however, retain at least the receptor binding domains with or without the regions involved in signal transduction.

There is considerable literature on variants of the glycoprotein hormones and it is clear that a large number of possible variants which result both in agonist and antagonist activity can be prepared. Such variants are disclosed, for example, in Chen, F. et al. *Molec Endocrinol* (1992) 6:914-919; Yoo, J. et al. *J Biol Chem* (1993) 268:13034-13042; Yoo, J. et al. *J Biol Chem* (1991) 266:17741-17743; Puett, D. et al. *Glycoprotein Hormones*, Lusbader, J. W. et al. EDS, *Springer Verlag* New York (1994) 122-134; Kuetmann, H. T. et al. (ibid.) pages 103-117; Erickson, L. D. et al. *Endocrinology* (1990) 126:2555-2560; and Bielinska, M. et al. *J Cell Biol* (1990) 111:330a (Abstract 1844).

Other variants include those wherein one or more cystine-bond is deleted, typically by substituting a neutral amino acid for one or both cysteines which participate in the link. Particularly preferred cystine bonds which may be deleted are those between positions 26 and 110 and between positions 23 and 72.

In addition, it has been demonstrated that the β subunits of the hormone quartet can be constructed in chimeric forms so as to provide biological fulnctions of both components of the chimera, or, in general, hormones of altered biological function. Thus, chimeric molecules which exhibit both FSH and LH/CG activities can be constructed as described by Moyle, *Proc Natl Acad Sci* (1991) 88:760-764; Moyle, *Nature* (1994) 368:251-255. As disclosed in these papers, substituting amino acids 101-109 of FSH-β for the corresponding residues in the CG-β subunit yields an analog with both hCG and FSH activity.

As used herein "peptide" and "protein" are used interchangeably, since the length distinction between them is arbitrary.

As stated above, the "variants" employed as α and β subunits in forming compound of the invention with or without linking moieties may represent the complete amino acid sequences of the subunits or only portions thereof.

"Variants" also include α and/or β chains which contain a CTP (or a variant of CTP) inserted into a noncritical region.

"Variants" may be agonists or antagonists of the hormone containing the corresponding native β subunit—i.e., a "variant" of the LH β subunit will confer agonist or antagonist activity to LH. The agonist activity may be the same as that of the native β subunit or may be enhanced or decreased.

"Noncritical" regions of the α and β subunits are those regions of the molecules not required for biological activity (including agonist and antagonist activity). In general, these regions are removed from binding sites, precursor cleavage sites, and catalytic regions. Regions critical for inducing proper folding, binding to receptors, catalytic activity and the like should be evaluated. It should be noted that some of the regions which are critical in the case of the α and β interaction in the dimer become noncritical in single-chain units since the conformational restriction imposed by the molecule may obviate the necessity for these regions. The ascertainment of noncritical regions is readily accomplished by deleting or modifying candidate regions and conducting an appropriate assay for the desired activity. Regions where modifications result in loss of activity are critical; regions wherein the alteration results in the same or similar activity (including antagonist activity) are considered noncritical.

It should again be emphasized that by "activity" is meant activity which is either agonistic or antagonistic to that of the corresponding native hormone. Thus, certain regions are critical for behavior of a variant as an antagonist, even though the antagonist is unable to directly provide the physiological effect of the hormone.

For example, for the α subunit, positions 33-59 are thought to be necessary for signal transduction and the 20 amino acid stretch at the carboxy terminus is needed for signal transduction/receptor binding. Residues critical for assembly with the β subunit include at least residues 33-58, particularly 37-40.

Where the noncritical region is "proximal" to the N- or C-terminus, the insertion is at any location within 10 amino acids of the terminus, preferably within 5 amino acids, and most preferably at the terminus per se.

As used herein, the "CTP unit" refers to an amino acid sequence found at the carboxy terminus of human chorionic gonadotropin β subunit which extends from amino acid 112-118 to residue 145 at the C-terminus or to a portion thereof. Thus, each "complete" CTP unit contains 28-34 amino acids, depending on the N-terminus of the CTP.

By a "partial" CTP unit is meant an amino acid sequence which occurs between positions 112-118 to 145 inclusive, but which has at least one amino acid deleted from the shortest possible "complete" CTP unit (i.e. from positions 118-145). These "partial" sequences are included in the definition of "variants." The "partial" CTP units preferably contain at least one O-glycosylation site. The CTP unit contains four glycosylation sites at the serine residues at positions 121 (site 1); 127 (site 2); 132 (site 3); and 138 (site 4). The partial forms of CTP useful in agonists will contain one or more of these sites arranged in the order in which they appear in the native CTP sequence, although intervening sites may be omitted. Some nonglycosylated forms of the hormones are antagonists and are useful as such.

In some cases, CTP units may be inserted or used as linkers in tandem. By "tandem" inserts or extensions is meant that the insert or extension contains at least two. "CTP units." Each CTP unit may be complete or a fragment, and native or a variant. All of the CTP units in the tandem extension or insert may be identical, or they may be different from each other.

The "linker " is a moiety that joins the α and β sequences without interfering with the activity that would otherwise be exhibited by the same α and β chains as members of a hormone, or which alters that activity to convert it from agonist to antagonist activity. The level of activity may change within a reasonable range, but the presence of the linker cannot be such so as to deprive the single-chain hormone of substantial agonist or substantial antagonist activity. The single-chain forms must exhibit activity pertinent to the hormonal activity of the native hormones, the elements of which form their components.

As used herein, "≈" or "noncovalent link" means a noncovalent link that exists between the α subunit covalently linked to the $\beta^1$ subunit and an additional $\beta^2$ subunit.

Preferred Embodiments of the Differentially Acting Glycoprotein Hormones

The compounds of the invention are most efficiently and economically produced using recombinant techniques. Therefore, single-chain proteins comprising those forms of α and β chains, CTP units and other linker moieties which include only gene-encoded amino acids are preferred. It is possible, however, as set forth above, to construct at least portions of the single-chain hormones using synthetic peptide techniques or other organic synthesis techniques and therefore variants which contain nongene-encoded amino acids and nonpeptide based linkers are also within the scope of the invention.

In one preferred embodiment, the C-terminus of the $\beta^1$ subunit is covalently linked, optionally through a linker, to the N-terminus of the mature $\alpha$ subunit which is in turn covalently linked optionally through a linker to the $\beta^2$ subunit. The linkage can be a direct peptide linkage wherein the C-terminal amino acid of one subunit is directly linked through the peptide bond to the N-terminus of the other; however, in many instances it is preferable to include a linker moiety between the two termini. In many instances, the linker moiety will provide at least one $\beta$ turn between the two chains. The presence of proline residues in the linker may therefore be advantageous.

(It should be understood that in discussing linkages between the termini of the subunits comprising the single chain forms, one or more termini may be altered by substitution and/or deletion as described above.)

In one particularly preferred set of embodiments, the linkage is head-to-tail and the linker moiety will include one or more CTP units and/or variants or truncated forms thereof. Preferred forms of the CTP units used in such linker moieties are described hereinbelow.

In addition to their occurrence in the linker moiety, CTP and its variants may also be included in any noncritical region of the subunits making up the single-chain hormone as described above.

While CTP units are preferred inclusions in the linker moiety, it is understood that the linker may be any suitable covalently bound material which provides the appropriate spatial relationship between the $\alpha$ and $\beta$ subunits. Thus, for head-to-tail configurations the linker may generally be a bivalent moiety such as a peptide comprising an arbitrary number, but typically less than 100, more preferably less than 50 amino acids which has the proper hydrophilicity/hydrophobicity ratio to provide the appropriate spacing and conformation in solution or a nonpeptide linker which confers these characteristics. In general, the linker should be on balance hydrophilic so as to reside in the surrounding solution and out of the way of the interaction between the $\alpha$ and $\beta$ subunits or the two $\beta$ subunits. It is preferable that the linker include $\beta$ turns typically provided by proline residues in peptide linkers, or comprise serine and/or glycine residues. Any suitable polymer, including peptide linkers, with the above-described correct characteristics may be used.

Particularly preferred embodiments of the single-chain forms of the invention include in head-to-tail configuration:

βFSH-α-βFSH; α-βFSH-βLH; βFSH-α-βLH;

βLH-α-βLH; α-βLH-βFSH; βLH-α-βFSH;

βTSH-α-βTSH; βTSH-βFSH-α; βTSH-α-βFSH;

βCG-α-βCG; α-βCG-βFSH; α-βCG-βTSH; βCG-βFSH-α; βCG-α-βTSH;

βFSH-CTP-αβFSH; α-βFSH-CTP-βLH; βFSH-CTP-α-βLH;

βLH-CTP-αβLH; α-βLH-CTP-βFSH; βLH-α-CTP-βFSH;

βLH(δ115-123)-α-βFSH; βLH(δ115-123)-CTP-α-βFSH;

βCG-CTP-α CTP-βFSH-CTP-CTP;

βTSH-CTP-CTP-αβFSH-CTP-CTP;

βFSH-CTP-CTP-α-βLH; βLH-CTP-CTP-βLH-α;

βCG-CTP-CTP-α-βTSH; βCG-CTP-CTP-βLH-α;

βFSH-CTP-βLH(δ115-123)-CTP-α;

and the like. Also particularly preferred are the human forms of the subunits. In the above constructions, "CTP" refers to CTP or its variants including truncations as described in PCT application WO96/05224.

In one embodiment, the C-terminus of the $\beta^1$ subunit is covalently linked, optionally through a linker, to the N-terminus of the mature $\alpha$ subunit which is in turn is noncovalently linked to an additional $\beta^2$ subunit. The $\alpha$ and $\beta$ subunits in the single-chain form of the present invention allow for the non-covalent linkage of an additional $\beta$ subunit to the tethered $\alpha$ subunit. Particularly preferred embodiments of the compositions of formulas (4) and (5) for use in the method of the invention include in head-to-tail configuration (for the single-chain component):

βFSH-α≈βFSH; βFSH-α≈βCG; βFSH-α≈βLH; βFSH-α≈βTSH

βCG-α≈βCG; βCG-α≈βFSH; βCG-α≈βLH; βCG-α≈βTSH

βLH-α≈βLH; βLH-α≈βFSH; βLH-α≈βCG; βLH-α≈βTSH

βTSH-α≈βTSH; βTSH-α≈βCG; βTSH-α≈βLH; βTSH-α≈βFSH;

βFSH≈α-βFSH; βCG≈α-βCG; βLH≈α-βFSH; βTSH≈α-βFSH;

βCG≈α-βCG; βFSH≈α-βCG; βLH≈α-βCG; βTSH≈α-βCG;

βLH≈α-βLH; βFSH≈α-βLH; βCG≈α-βLH; βTSH≈α-βLH;

βTSH≈α-βTSH; βCG≈α-βTSH; βLH≈α-βTSH; βFSH≈α-βTSH.

and the like. Therefore, in one embodiment of the invention, the tethered β subunit and the additional β subunit will differ from one another. For example, if the tethered β subunit is a β subunit of FSH or a variant and the noncovalently linked β subunit is the β subunit of CG or a variant, the resulting compound will have the ability to act upon the FSH and CG receptors simultaneously. The noncovalently linked β subunit may have agonist or antagonist activity, independent of the activity of the tethered β subunit. Additionally, the additional β subunit may have a different circulating half-life from that of the tethered β subunit. This difference in the circulating half-lives of the β subunits allows for varying degrees of activity with respect to time.

Another preferred embodiment of the invention is where the additional β subunit and the tethered β subunit are the same or variants of each other. For example, a covalently linked FSHβ subunit and an additional noncovalently linked βFSH subunit. An embodiment of this type would have the effect of increasing the agonist or antagonist activity. The activity would greatest during the duration of the shorter circulating half-life. Due to the longer circulating half-life of the tethered β subunit (when the β subunits are otherwise identical), when the noncovalently linked β subunit is no longer effective, the single-chain form will still have activity but to a lesser degree.

Another embodiment of the invention is where one β subunit is mutated to have reduced or greater activity than the other β subunit. For example, a tethered β subunit having LH antagonist activity in combination with a β subunit having FSH agonist activity would have the effect of increasing the FSH/LH ratio suitable for follicle development and fertility. If a shorter circulating half-life of the LH activity is desired, then the tethered β subunit would have FSH activity and the other β subunit would have LH activity.

While for human use, the human forms of the α and β subunits are desirable, it should be noted that the corresponding forms in other vertebrates are useful in veterinary contexts. Thus, the FSH, TSH and LH subunits characteristic of bovine, ovine, equine, porcine, feline, canine, and other species are appropriate to indications affecting these species per se.

In some embodiments, an additional drug may be included in the linker moiety. Such drugs may be peptides or proteins such as insulin-like growth factors; epidermal growth factors; acidic and basic fibroblast growth factors; platelet-derived growth factors; the various colony stimulating factors, such as granulocyte CSF, macrophage-CSF, and the like; as well as the various cytokines such as IL-2, IL-3 and the plethora of additional interleukin proteins; the various interferons; tumor necrosis factor; and the like. Suitable cleavage sites for the release of these drugs may be included, such as target sequences for proteases whose target sites are not present in the α and β subunits. Peptide- or protein-based drugs have the advantage that the entire construct can readily be produced by recombinant expression of a single gene. Also, small molecule drugs such as antibiotics, antiinflammatories, toxins, and the like can be used.

In general, the drugs included within the linker moiety will be those desired to act in the proximity of the receptors to which the hormones ordinarily bind. Suitable provision for release of the drug from inclusion within the linker will be provided, for example, by also including sites for enzyme-catalyzed lysis as further described under the section headed Preparation Methods hereinbelow.

In addition, if desired, the amount of time that the drug is active and circulating can be limited to the shorter circulating half-life of the noncovalently linked β subunit. This may be achieved by including the drug within the noncovalently linked β subunit rather than within the single-chain form.

Other Modifications

The compounds of the invention may be further conjugated or derivatized in ways generally understood to derivatize amino acid sequences, such as phosphorylation, glycosylation, deglycosylation of ordinarily glycosylated forms, acylation, modification of the amino acid side chains (e.g., conversion of proline to hydroxyproline) and similar modifications analogous to those posttranslational events which have been found to occur generally.

The glycosylation status of the hormones of the invention is particularly important. The hormones may be prepared in nonglycosylated form either by producing them in procaryotic hosts or by mutating the glycosylation sites normally present in the subunits and/or any CTP units that may be present. Both nonglycosylated versions and partially glycosylated versions of the hormones can be prepared by manipulating the glycosylation sites. Normally, glycosylated versions are, of course, also included within the scope of the invention.

As is generally known in the art, the compounds of the invention may also be coupled to labels, carriers, solid supports, and the like, depending on the desired application. The labeled forms may be used to track their metabolic fate; suitable labels for this purpose include, especially, radioisotope labels such as iodine 131, technetium 99, indium 111, and the like. The labels may also be used to mediate detection of the single-chain proteins in assay systems; in this instance, radioisotopes may also be used as well as enzyme labels, fluorescent labels, chromogenic labels, and the like. The use of such labels permits localization of the relevant receptors since they can be used as targeting agents for such receptors.

The compounds of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of bifunctional linkers, can be employed.

Similar linking techniques, along with others, may be employed to couple the proteins of the invention to solid supports. When coupled, these proteins can then be used as affinity reagents for the separation of desired components with which specific reaction is exhibited. Thus, they are useful in the purification and isolation of the receptors with which the appropriate β subunit interacts.

Preparation Methods

Methods to construct the compounds of the invention are well known in the art. As set forth above, if only gene encoded amino acids are included, and the single-chain form is in a head-to-tail configuration, the most practical approach at present is to synthesize these materials recombinantly by expression of the DNA encoding the desired protein or proteins. DNA containing the nucleotide sequence encoding the single-chain forms included in the invention compositionss, including variants, can be prepared from native sequences, or synthesized de novo or using combinations of these techniques. Techniques for site-directed mutagenesis, ligation of additional sequences, amplification such as by PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available compatible with a wide variety of hosts, including procaryotic hosts such as *E. coli* or *B. subtilis* and eucaryotic hosts such as yeast, other fungi such as *Aspergillus* and *Neurospora*, plant cells, insect cells, mammalian cells such as CHO cells, avian cells, and the like.

The choice of host is particularly pertinent to posttranslational events, most particularly including glycosylation. The location of glycosylation is mostly controlled by the nature of the glycosylation sites within the molecule; however, the nature of the sugars occupying this site is largely controlled by the nature of the host. Accordingly, a fine-tuning of the properties of the hormones of the invention can be achieved by proper choice of host.

A particularly preferred form of gene for the α subunit portion, whether the α subunit is modified or unmodified, is the "minigene" construction. As used herein, the α subunit "minigene" refers to the gene construction disclosed in Matzuk, M. M., et al., *Mol Endocrinol* (1988) 2:95-100, in the description of the construction of $pM^2/CG\alpha$ or $pM^2/\alpha$ For recombinant production, modified host cells using expression systems are used and cultured to produce the desired protein. These terms are used herein as follows:

A "modified" recombinant host cell, i.e., a cell "modified to contain" the recombinant expression systems of the invention, refers to a host cell which has been altered to contain this expression system by any convenient manner of introducing it, including transfection, viral infection, and so forth. "Modified cells" refers to cells containing this expression system whether the system is integrated into the chromosome or is extrachromosomal. The "modified cells" may either be stable with respect to inclusion of the expression system or the encoding sequence may be transiently expressed. In short, recombinant host cells "modified" with the expression system of the invention refers to cells which include this expression system as a result of their manipulation to include it, when they natively do not, regardless of the manner of effecting this incorporation.

"Expression system" refers to a DNA molecule which includes a coding nucleotide sequence to be expressed and those accompanying control sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

Secretion of the protein produced is generally desired. Thus, nucleotide sequences encoding a signal peptide are also included so as to produce the signal peptide operably linked to the desired single-chain hormone to produce the preprotein, which upon secretion, is cleaved to release the mature single-chain hormone or desired β subunit. Glycoprotein hormones are normally secreted proteins and the signal sequences included may be those associated with the hormones per se or may be heterologous thereto. Although not preferred, intracellular production of the hormones could be effected by suitable manipulation of the encoding genes.

As used herein "cells," "cell cultures," and "cell lines" are used interchangeably without particular attention to nuances of meaning. Where the distinction between them is important, it will be clear from the context. Where any can be meant, all are intended to be included.

The protein produced may be recovered from the lysate of the cells if produced intracellularly, or from the medium if secreted. Techniques for recovering recombinant proteins from cell cultures are well understood in the art, and these proteins can be purified using known techniques such as chromatography, gel electrophoresis, selective precipitation, and the like.

With respect to recombinant production of the compounds of formulas (1)-(3), a single expression system comprising the nucleotide sequence encoding the compounds of these formulas will be employed. For compositions of formulas (4) and (5), in general, two expression systems, both contained within the recombinant host, are preferably used. Thus, an expression system for the α-(linker)$_m$-β1 or β1-(linker)$_m$-α portion of the compound will be constructed containing the nucleotide sequence encoding this single-chain peptide and an additional expression system encoding β$^2$ will also be included in the cell. The two expression systems may be contained on a single vector, within the chromosome of the host cell, on separate vectors, or one expression system may reside in the chromosome and the other on an extrachromosomally replicating vector. Alternatively, a dicistronic expression system containing both required encoding nucleotide sequences may be employed, either on an extrachromosomally replicating vector or contained in the host cell chromosome. In still another approach, the two noncovalently bound components may be prepared separately and associated under suitable in vitro conditions. Conditions favoring assembly of the compositions of formulas (4) or (5) would be familiar to those in the art and would mimic intracellular conditions.

In addition, all or a portion of the compounds of the invention may be synthesized directly using peptide synthesis techniques known in the art. Synthesized portions may be ligated, and release sites for any drug contained in the linker moiety introduced by standard chemical means. For those embodiments which contain amino acids which are not encoded by the gene and those embodiments wherein the head-to-head or tail-to-tail configuration is employed, of course, the synthesis must be at least partly at the protein level. Head-to-head junctions at the natural N-termini or at positions proximal to the natural N-termini may be effected through linkers which contain functional groups reactive with amino groups, such as dicarboxylic acid derivatives. Tail-to-tail configurations at the C-termini or positions proximal to the C-termini may be effected through linkers which are diamines, diols, or combinations thereof.

Antibodies

The proteins of the invention may be used to generate antibodies specifically immunoreactive with the multiple domain glycoprotein hormones disclosed herein. These antibodies are useful in a variety of diagnostic and therapeutic applications.

The antibodies are generally prepared using standard immunization protocols in mammals such as rabbits, mice, sheep or rats, and the antibodies are titered as polyclonal antisera to assure adequate immunization. The polyclonal antisera can then be harvested as such for use in, for example, immunoassays. Antibody-secreting cells from the host, such as spleen cells, or peripheral blood leukocytes, may be immortalized using known techniques and screened for production of monoclonal antibodies immunospecific with the proteins of the invention.

"Antibodies", which may be from any animal species, including humans, include any fragment which retains the required immunospecificity, such as $F_{ab}$, $F_{ab'}$, or $F_{(ab')_2}$, $F_v$ and so forth. Thus, the antibodies may also be prepared using recombinant techniques, typically by isolating nucleotide sequences encoding at least the variable regions of monoclonal antibodies with the appropriate specificity and constructing appropriate expression systems. This approach permits any desired modification such as production of $F_v$ forms, chimeric forms, "humanized" forms and the like.

By "immunospecific for the proteins of the invention" is meant antibodies which specifically bind the referent compound of the invention, but not the native glycoprotein hormones or any of the included subunits per se or any single-chain units which include only a single β subunit within the general parameters considered to determine affinity or nonaffinity. It is understood that specificity is a relative term, and an arbitrary limit could be chosen, such as a difference in specific binding of 100-fold or greater. Thus, an immunospecific antibody included within the invention is at least 100 times more reactive with the multiple domain complex than with the corresponding native hormone, prior art single-chain forms or separate subunits. Such antibodies can be obtained, for example, by screening for those that bind the invention compounds and discarding those that also bind the native hormones, subunits or prior art single-chain forms set forth in WO95/22340 and WO96/05224.

Formulation and Methods of Use

The proteins of the invention are formulated and administered using methods comparable to those known for the heterodimers generally corresponding to them. Thus, formulation and administration methods will vary according to the particular hormone or hormone combination used. However, the dosage level and frequency of administration may be altered as compared to the native heterodimers, especially if CTP units are present in view of the extended biological half-life due to its presence.

Formulations for proteins of the invention are those typical of protein or peptide drugs such as found in *Remington's Pharmaceutical Sciences*, latest edition, Mack Publishing Company, Easton, Pa. Generally, proteins are administered by injection, typically intravenous, intramuscular, subcutaneous, or intraperitoneal injection, or using formulations for transmucosal or transdermal delivery. Other modes of delivery, such as suppositories, may also be employed. These formulations generally include a detergent or penetrant such as bile salts, fusidic acids, and the like. These formulations can be administered as aerosols or suppositories or, in the case of transdermal administration, in the form of skin patches. Oral administration is also possible provided the formulation protects the peptides of the invention from degradation in the digestive system.

Optimization of dosage regimen and formulation is conducted as a routine matter and as generally performed in the art. These formulations can also be modified to include those suitable for veterinary use.

The compositions of the invention may be used in many ways, most evidently as substitutes for the native forms of the hormones. Thus, the compositions of the invention can be used in treatment of infertility, as aids in in vitro fertilization techniques, and other therapeutic methods associated with the native hormones or their subunits. These techniques are applicable to humans as well as to other animals. The choice of the composition in terms of its species derivation will, of course, depend on the subject to which the method is applied. It will be realized that the ability to act differentially which is conferred on the compositions of the invention confers opportunities for therapies that have previously been unavailable.

The invention compositions are also useful as reagents in a manner similar to that employed with respect to the native heterodimers.

In addition, the compounds of the invention may be used as diagnostic tools to detect the presence or absence of antibodies that bind to the native proteins to the extent such antibodies bind to the relevant portions of these multiple domain compounds in biological samples. They are also useful as control reagents in assay kits for assessing the levels of these hormones in various samples. Protocols for assessing levels of the hormones themselves or of antibodies raised against them are standard immunoassay protocols commonly known in the art. Various competitive and direct assay methods can be used involving a variety of labeling techniques including radio-isotope labeling, fluorescence labeling, enzyme labeling and the like.

The compounds of the invention are also useful in detecting and purifying receptors to which the native hormones bind. Thus, the compounds of the invention may be coupled to solid supports and used in affinity chromatographic preparation of receptors or antihormone antibodies. The resulting receptors are themselves useful in assessing hormone activity for candidate drugs in screening tests for therapeutic and reagent candidates. Of course, account must be taken of the dual specificity of the β subunits in any of these compounds where the β subunits are different. However, where the two β subunits are identical, they offer a powerful affinity purification tool for the relevant receptor.

Finally, the antibodies uniquely reactive with the compounds of the invention can be used as purification tools for isolation of these materials in their subsequent preparations. They can also be used to monitor levels of these compounds administered as drugs.

The following examples are intended to illustrate but not to limit the invention.

EXAMPLE 1

Preparation of CGβ-α-CTP-FSHβ

A nucleotide sequence encoding the title compound was prepared using the available nucleotide sequences for the relevant portions of the subunits. The CGβ region encodes the 145 amino acids of human CGβ; the α subunit-encoding nucleotide sequence encodes the 92 amino acids of human a as the minigene; the CTP-encoding sequence encodes 28 amino acids representing positions 118-145 of human chorionic gonadotropin; and the FSHβ encoding region encodes the 111 amino acids of the human FSHβ subunit.

An amplified fragment containing CGβ exon 3, the a minigene, CTP and βFSH was inserted into the SalI site of pM$^2$HA-CGβexon1,2 an expression vector which is derived from pM$^2$ and containing CGβ exons 1 and 2 in the manner described by Sachais, β *Biol Chem* (1993) 268:2319. pM$^2$ containing CGβ exons 1 and 2 is described in Matzuk, M. M. et al. *Proc Natl Acad USA* (1987) 84:6354-6358 and Matzuk, M. M. et al. *J Cell Biol* (1988) 106:1049-1059. First, a fragment containing the α minigene downstream of CGβ exon 3 was inserted into this vector to obtain pM$^2$-HACGβα. pM$^2$-HACGβα was then cleaved with ScaI and ligated with ScaI restricted pBIIKS(+)α-CTP-FSH. The resulting expression vector pM$^2$-HACGβ-α-CTP-FSH produces the title compound when inserted into a suitable host.

EXAMPLE 2

Production and Activity of the CGβ-α-CTP-FSHβ

The expression vector constructed in Example 1 was transfected into Chinese hamster ovary (CHO) cells and production of the protein was assessed by immunoprecipitation of radiolabeled protein on SDS gels.

The culture medium was collected, concentrated and tested for binding to the human LH receptor (expected to bind the βCG-α portion).

For this assay, the LH receptor was prepared by inserting the cDNA encoding the entire human LH receptor into the expression vector pCMX (Oikawa, J. X-C et al. *Mol Endocrinol* (1991) 5:759-768). Exponentially growing 293 cells were transfected with this vector using the method of Chen, C. et al. *Mol Cell Biol* (1987) 7:2745-2752, resulting in expression of the LH receptor at the surface.

In the assay, the cells expressing human LH receptor ($2 \times 10^5$/tube) were incubated with 1 ng of labeled hCG in competition with increasing concentrations of unlabeled hCG or increasing amounts of the sample to be tested at 22° C. for 18 hours. The decrease in label in the presence of sample measures the binding ability in the sample. In this assay, with respect to the human LH receptor in 293 cells, the heterodimeric hCG had an activity typical of wild-type as previously determined and the CGβ-α-CTP-FSHβ-containing medium also showed activity. These results are shown in FIG. 1. As shown, both heterodimeric (solid squares) hCG and the bifunctional single-chain protein of the invention (solid circles) competed successfully with labeled hCG for LH receptor. The bifunctional compound is less potent due to the modification of the α subunit carboxy terminus.

Also shown in FIG. 1 are the results of the assay wherein varying amounts of a culture supernatant derived from cells modified to contain two expression systems was tested. One expression system produced a single chain FSHβ-α; the other produced the β subunit of hCG. The resulting noncovalently associated single-chain FSHα-β/CGβ complex (solid triangles) also successfully competed for binding.

In a similar manner, the supernatant from the culture medium containing CGβ-α-CTP-FSHβ was tested for binding to the receptor for FSH, expressed in 293 cells. The assay was conducted in the manner described above, except that cells expressing the human FSH receptor were substituted for those expressing human LH receptor and labeled FSH was used as the competitor. The results of this assay are shown in FIG. 2.

As shown, the single-chain title compound (solid circles) competed successfully with FSH (solid squares) for binding. In an unrelated experiment, also shown in FIG. 2, the mixture of a different type of complex—i.e., single-chain FSHβ-α noncovalently associated with CGβ—which is mixed with uncomplexed excess single-chain FSHβ-α (solid triangles), was an excellent competitor.

EXAMPLE 3

Construction of Additional Expression Vectors

In a manner similar to that set forth in Example 1, expression vectors for the production of single-stranded bifunctional FSHβ-CTP-α-CG β; α-FSHβ-CTP-CG β, CG β-βFSH-CTP-α, and βLH-CTP-βFSH-CTP-α are prepared and transfected into CHO cells. The culture supernatants are cultured and tested as described above with respect both to the LH and FSH receptors. These compounds, too, show ability to bind both receptors.

EXAMPLE 4

Preparation of FSHβ-α≈CGβ

To create the compound, FSHβ-α≈CGβ, the expression vectors for the production of a single-chain FSHβ-α, and a human CGβ subunit were prepared and co-transfected into Chinese hamster ovary (CHO) cells in a manner similar to the methods disclosed in the PCT application of the inventor herein, WO96/05224 published 22 Feb. 1996. The CGβ subunit combined with FSHβ-α to form a noncovalent FSHβ-α≈CG complex. The production and activity of the noncovalent FSHβ-α≈CG complex was assessed by immunoprecipitation of radiolabeled protein on SDS gels.

The culture medium was collected, concentrated and tested for binding to the human LH receptor (expected to bind the βCG portion) and the human FSH receptor (expected to bind the FSHβ-α).

The results indicate that the noncovalent FSHβ-α≈CG complex displays CG and FSH-specific receptor binding. These data indicate that the α subunit of the tether, although covalently linked to the FSHβ domain, can functionally interact with a different β subunit and the presence of this configuration does not abolish bioactivity. Other multiple domain complexes such as βFSH-α≈βLH, βCG-α≈βLH, βLH-α≈βTSH, and βTSH-α≈βFSH may also be generated in a similar fashion.

EXAMPLE 5

Use of Differentially Acting Compounds to Regulate Hormone Ratios

The differentially acting compounds are formulated and administered using methods comparable to those known for the native hormones corresponding to them.

A. Increasing fertility by increasing the FSH/LH ratio and/or by increasing CG.

Increased fertility may be achieved by increasing the FSH/LH ratio with a compound of the formula (1)-(5) wherein one β subunit has weakened LH agonist activity or LH antagonist activity and the other β subunit has (optionally enhanced) FSH agonist activity. The LHβ subunit may be modified to have lower agonist or antagonist activity by eliminating glycosylation of the LHβ chain or by point mutations, whereas the FSHβ subunit may be used in its native form or modified to have increased agonist activity. The resulting compound will have the ability to increase FSH hormone levels while simultaneously decreasing LH hormone levels. When a therapeutic dose of this compound is administered to a mammal during the follicular phase of the menstrual cycle, increased fertility results.

Additionally, it may be advantageous to make the circulating half-life of the FSH subunit longer than the LHβ circulating half-life. This is aided by using a FSHβ-α≈LHβ compound.

Increased fertility may also be achieved by increasing CG hormone levels and decreasing LH hormone levels by administering a compound of the formula (1)-(5) wherein one β subunit has LH antagonist activity or lowered LH agonist activity and the other β subunit has CG agonist activity. Additionally, the CGβ subunit may be engineered to have a greater binding affinity than LHβ to the CG/LH receptor. When administered at appropriate times and doses, the FSH/LH ratio will increase to ratio favorable for fertility and the CG activity will also increase to levels favorable for pregnancy.

Likewise, fertility may be increased with a compound of the formula (1)-(5) wherein one β subunit has FSH agonist activity and the other β subunit has CG agonist activity. Administration of these complexes will increase the FSH/LH ratio favorable for fertility and also increase CG activity to levels favorable for pregnancy.

It may be advantageous to make the circulating half-life of one β subunit longer than the other, which is aided by using a composition of the formula (4) or (5).

B. Inducing infertility by decreasing the FSH/LH ratio and/or decreasing CG.

Infertility may be induced by decreasing the FSH/LH ratio with the administration of a compound of the formula (1)-(5) wherein one β subunit has LH agonist activity and the other β subunit has FSH antagonist or reduced agonist activity. For this application, the LHβ subunit may be modified to have enhanced agonist activity by altering the glycosylation of the LHβ chain or by point mutations, whereas the FSHβ subunit may be modified to have lowered agonist activity. The resulting compound will have the ability to increase LH activity while simultaneously decreasing FSH activity, thereby lowering the FSH/LH ratio to a level unfavorable for fertility.

Infertility may also be induced by decreasing the FSH/LH ratio with the administration of a compound of the formula (1)-(5) wherein one β subunit has LH agonist activity and the other β subunit has CG agonist activity. Administration of this compound would result in a low FSH/LH ratio and a high CG hormone level, both of which are unfavorable for fertility and pregnancy.

As above, it may be advantageous to make the circulating half-life of one β subunit longer than the other, by using a composition of the formula (4) or (5). It may also be advantageous to vary the binding affinities of the β subunits.

C. Treating polycystic ovarian syndrome by decreasing the LH/FSH ratio.

Polycystic ovarian syndrome is characterized by incomplete follicle development and abnormal ovulation. Women suffering from this disease have elevated androgens and a high ratio of LH/FSH relative to normal fertile women. Thus, at the time of the menstrual cycle when follicular development is supposed to be normally initiated, administration of a compound of the formula (1)-(5) wherein one β subunit has lowered LH agonist activity or antagonist activity and the other β subunit has FSH agonist activity will boost follicle development and induce ovulation. Since the administration of an FSH agonist has the risk of causing hyperstimulation, it is preferable that FSHβ subunit is the noncovalently linked β subunit having the shorter circulating half-life and/or the FSHβ subunit is engineered to have a decreased binding affinity.

The invention claimed is:

1. An isolated glycosylated or nonglycosylated composition of the formula

 (1); or

 (2)

wherein each of $\beta^1$ and $\beta^2$ has the amino acid sequence of the β subunit of a vertebrate glycoprotein hormone, or a variant thereof;

"α" has the amino acid sequence of the α subunit of a vertebrate glycoprotein hormone or a variant thereof;

"linker" is a linker moiety; and

"≈" is a noncovalent link between α and $\beta^2$;

m is 0 or 1;

wherein one of $\beta^1$ and $\beta^2$ confers agonist activity and the other confers antagonist activity.

2. The composition of claim 1, wherein $\beta^1$ and $\beta^2$ are β subunits of different glycoprotein hormones or variants thereof.

3. The composition of claim 1, wherein $\beta^1$ and $\beta^2$ exhibit different biological half-lives.

4. The composition of claim 1, wherein
one of $\beta^1$ and $\beta^2$ confers FSH agonist activity and the other confers LH antagonist activity; or
wherein one of $\beta^1$ and $\beta^2$ confers LH antagonist activity and the other confers CG agonist activity.

5. The composition of claim 1, wherein
one of $\beta^1$ and $\beta^2$ confers FSH antagonist activity and the other confers LH agonist activity; or
wherein one of $\beta^1$ and $\beta^2$ confers FSH antagonist activity and the other confers CG antagonist activity; or
wherein one of $\beta^1$ and $\beta^2$ confers LH agonist activity and the other confers CG antagonist activity.

6. The composition of claim 1, wherein one of $\beta^1$ and $\beta^2$ confers FSH agonist activity and the other confers LH antagonist activity.

7. A pharmaceutical formulation which consists essentially of an effective amount of the composition of claim 1 in admixture with at least one pharmaceutically acceptable excipient.

* * * * *